US011918433B2

(12) United States Patent
Mandanici et al.

(10) Patent No.: US 11,918,433 B2
(45) Date of Patent: *Mar. 5, 2024

(54) SURFACE TREATMENT FOR AN IMPLANT SURFACE

(71) Applicant: BIOMET 3I, LLC, Palm Beach Gardens, FL (US)

(72) Inventors: Daniel Mandanici, Loxahatchee, FL (US); Zachary B. Suttin, West Palm Beach, FL (US); Keng-Min Lin, San Mateo, CA (US); Olga S. Sanchez, Wellington, FL (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 1111 days.

This patent is subject to a terminal disclaimer.

(21) Appl. No.: 16/547,142

(22) Filed: Aug. 21, 2019

(65) Prior Publication Data
US 2019/0374311 A1 Dec. 12, 2019

Related U.S. Application Data

(63) Continuation of application No. 16/036,537, filed on Jul. 16, 2018, now Pat. No. 10,426,577, which is a (Continued)

(51) Int. Cl.
*A61C 8/00* (2006.01)
*A61C 13/00* (2006.01)
(Continued)

(52) U.S. Cl.
CPC .......... *A61C 8/0015* (2013.01); *A61C 8/0075* (2013.01); *A61C 13/0007* (2013.01);
(Continued)

(58) Field of Classification Search
CPC ....... A61C 8/0015; A61C 8/0075; C23F 1/30; A61B 17/86
See application file for complete search history.

(56) References Cited

U.S. PATENT DOCUMENTS 5,727,943 A 3/1998 Beaty et al.
5,876,453 A 3/1999 Beaty
(Continued)

FOREIGN PATENT DOCUMENTS

CN 103654979 3/2014
CN 108024844 A 5/2018
(Continued)

OTHER PUBLICATIONS

U.S. Appl. No. 15/233,553, U.S. Pat. No. 10,022,232, filed Aug. 10, 2016, Surface Treatment for an Implant Surface.
(Continued)

*Primary Examiner* — Dah-Wei D. Yuan
*Assistant Examiner* — Andrew J Bowman
(74) *Attorney, Agent, or Firm* — Sheridan Ross P.C.

(57) ABSTRACT

An implant system and a method of forming the implant system including an implant to be implanted into living bone. The implant includes titanium. The implant includes a first surface geometry on a first portion of a surface of the implant and a second surface geometry on a second portion of the surface of the implant. The first surface geometry includes at least a submicron topography including tube-like structures and the second surface geometry includes a first micro-scale topography, a second micro-scale topography superimposed on the first topography, and a submicron topography superimposed on the first and second micro-scale topographies, the submicron topography including the tube-like structures.

15 Claims, 11 Drawing Sheets

Related U.S. Application Data continuation-in-part of application No. 15/233,553, filed on Aug. 10, 2016, now Pat. No. 10,022,232.

(60) Provisional application No. 62/203,733, filed on Aug. 11, 2015.

(51) Int. Cl.
| | | |
|---|---|---|
| *C23F 1/30* | (2006.01) | |
| *A61L 27/10* | (2006.01) | |
| *A61L 27/28* | (2006.01) | |

(52) U.S. Cl.
CPC ............ *A61C 13/0012* (2013.01); *C23F 1/30* (2013.01); *A61C 8/0022* (2013.01); *A61C 2008/0046* (2013.01); *A61C 8/006* (2013.01); *A61C 8/0062* (2013.01); *A61L 27/10* (2013.01); *A61L 27/28* (2013.01); *A61L 2400/18* (2013.01)

(56) References Cited

U.S. PATENT DOCUMENTS

| | | | |
|---|---|---|---|
| 5,902,109 | A | 5/1999 | Reams, III et al. |
| 8,399,008 | B2 | 3/2013 | Webster et al. |
| 8,414,908 | B2 | 4/2013 | Jin et al. |
| 9,005,648 | B2 | 4/2015 | Jin et al. |
| 9,327,056 | B2 | 5/2016 | Bandyopadhyay et al. |
| 9,555,159 | B2 | 1/2017 | Jin et al. |
| 9,844,657 | B2 | 12/2017 | Jin et al. |
| 10,022,232 | B2 * | 7/2018 | Mandanici ............ A61B 17/86 |
| 10,426,577 | B2 * | 10/2019 | Mandanici ................. C23F 1/30 |
| 2004/0265780 | A1 | 12/2004 | Robb et al. |
| 2007/0110890 | A1 | 5/2007 | Berckmans, III et al. |
| 2007/0112353 | A1 | 5/2007 | Berckmans, III et al. |
| 2007/0187253 | A1 | 8/2007 | Gilbert et al. |
| 2008/0220394 | A1 | 9/2008 | Berckmans, III et al. |
| 2009/0035722 | A1 | 2/2009 | Balasundaram et al. |
| 2009/0220561 | A1 | 9/2009 | Jin et al. |
| 2009/0232870 | A1 | 9/2009 | Srivastava et al. |
| 2010/0028387 | A1 | 2/2010 | Balasundaram et al. |
| 2010/0187172 | A1 | 7/2010 | Paulose et al. |
| 2010/0318193 | A1 | 12/2010 | Desai et al. |
| 2011/0085968 | A1 | 4/2011 | Jin et al. |
| 2011/0159070 | A1 | 6/2011 | Jin et al. |
| 2011/0233169 | A1 | 9/2011 | Mayfield et al. |
| 2011/0236435 | A1 | 9/2011 | Biris |
| 2012/0010599 | A1 | 1/2012 | Jin et al. |
| 2014/0011020 | A1 | 1/2014 | Mertens et al. |
| 2014/0083494 | A1 | 3/2014 | Jung et al. |
| 2014/0086962 | A1 | 3/2014 | Jin et al. |
| 2014/0328999 | A1 | 11/2014 | Aizenberg et al. |
| 2014/0335617 | A1 | 11/2014 | Mukhopadhyay |
| 2017/0042682 | A1 | 2/2017 | Mandanici et al. |
| 2017/0197015 | A1 | 7/2017 | Desai et al. |
| 2017/0258960 | A1 | 9/2017 | Jin et al. |
| 2018/0318049 | A1 | 11/2018 | Mandanici et al. |

FOREIGN PATENT DOCUMENTS

| | | |
|---|---|---|
| JP | H08-140997 | 6/1996 |
| JP | H11-511662 | 10/1999 |
| JP | 2004-337616 | 12/2004 |
| JP | 2010-536534 | 12/2010 |
| JP | 2018522682 A | 8/2018 |
| WO | WO-2017027593 A1 | 2/2017 |

OTHER PUBLICATIONS

U.S. Appl. No. 16/036,537, filed Jul. 16, 2018, Surface Treatment for an Implant Surface.

Intention to Grant for European Patent Application No. 19745939.9, dated Mar. 18, 2022 42 pages.

Official Action with English Translation for Japan Patent Application No. 2018-506949, dated Apr. 12, 2022 6 pages.

"U.S. Appl. No. 15/233,553, Notice of Allowance dated Mar. 16, 2018", 12 pgs.

"U.S. Appl. No. 15/233,553, Response filed Jan. 16, 2018 to Restriction Requirement dated Nov. 13, 2017", 7 pgs.

"U.S. Appl. No. 15/233,553, Restriction Requirement dated Nov. 13, 2017", 6 pgs.

"U.S. Appl. No. 16/036,537, Non Final Office Action dated Nov. 19, 2018", 7 pgs.

"U.S. Appl. No. 16/036,537, Notice of Allowance dated May 20, 2019", 8 pgs.

"U.S. Appl. No. 16/036,537, Response filed Feb. 19, 2019 to Non Final Office Action dated Nov. 19, 2018", 8 pgs.

"International Application Serial No. PCT/US2016/046354, International Preliminary Report on Patentability dated Feb. 22, 2018", 7 pgs.

"International Application Serial No. PCT/US2016/046354, International Search Report dated Dec. 5, 2016", 4 pgs.

"International Application Serial No. PCT/US2016/046354, Written Opinion dated Dec. 5, 2016", 5 pgs.

Intention to Grant (2nd) for European Patent Application No. 19745939.9, dated Sep. 19, 2022 42 pages.

Official Action (with English Translation) for Japan Patent Application No. 2018-506949, dated Aug. 23, 2022 3 pages.

Notice of Allowance (with English Translation) for Japan Patent Application No. 2018-506949, dated Nov. 11, 2022 5 pages.

\* cited by examiner

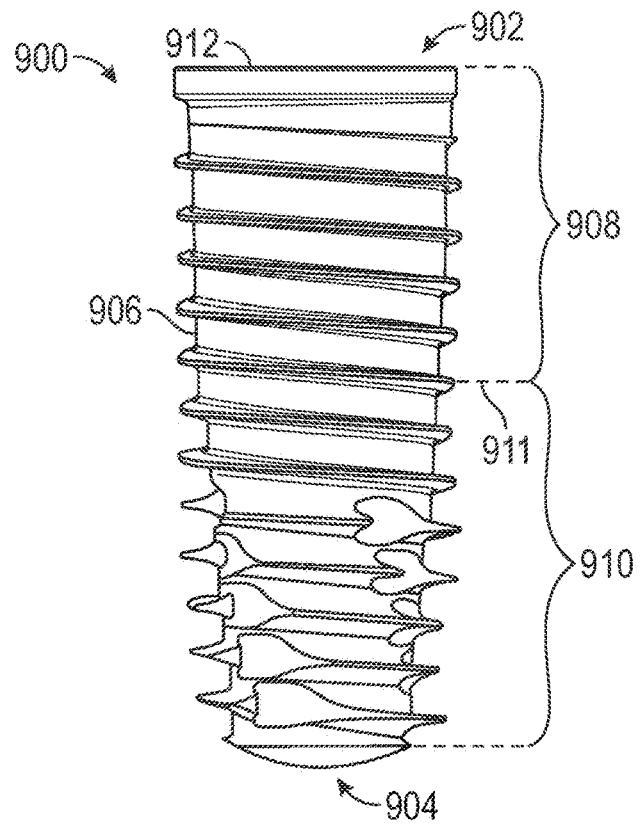
*Fig. 9*
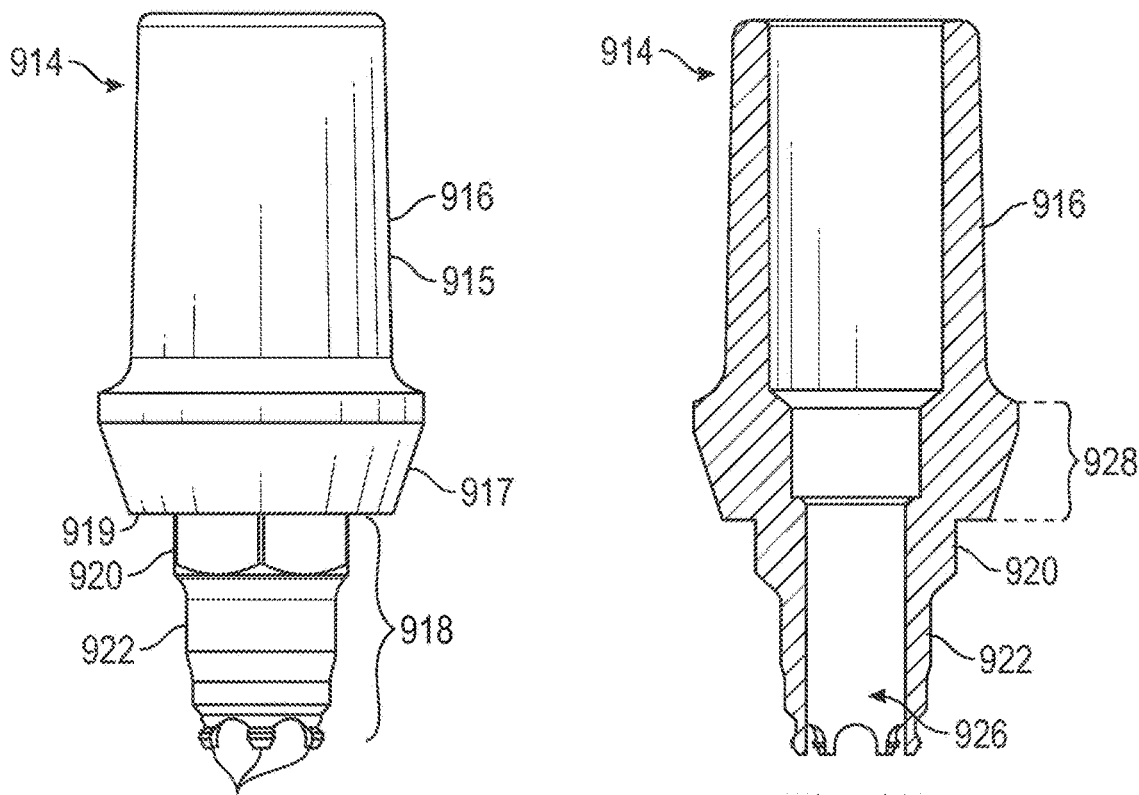
*Fig. 10a*  *Fig. 10b*

SURFACE TREATMENT FOR AN IMPLANT SURFACE

CLAIM OF PRIORITY

This application is continuation of U.S. patent application Ser. No. 16/036,537, filed Jul. 16, 2018, which is a continuation-in-part of U.S. patent application Ser. No. 15/233,553, filed Aug. 10, 2016, titled "SURFACE TREATMENT FOR AN IMPLANT SURFACE", now issued as U.S. Pat. No. 10,022,232, which claims the benefit claims the benefit of U.S. Provisional Patent Application Ser. No. 62/203,733, filed on Aug. 11, 2015, the benefit of priority of which is claimed hereby, and which is incorporated by reference herein in its entirety.

FIELD OF THE INVENTION

This invention relates generally to implants and, in particular, to dental implants having a layer of topographical complexities in the coarse-micron, fine-micron, and submicron ranges, respectively.

BACKGROUND OF THE INVENTION

It is becoming more common to replace a missing tooth with a prosthetic tooth that is placed upon and attached to a dental implant. Dental implants are often comprised of metal and metal alloys, including titanium (Ti) and titanium alloys. The dental implant serves as an artificial root that integrates with the gingiva and the bone tissue of the mouth.

For the dental implant to function successfully, sufficient osseointegration is required. In other words, a bond between the implant and the bone must be formed and retained. The surface of the implant may be roughened to help enhance the osseointegration process. Non-limiting examples of processes for roughening an implant surface include acid etching and grit blasting, which impart roughness on the surface.

Other existing techniques involve forming a generally thin (e.g., generally less than 10 microns) coating of osseointegration materials, such as hydroxyapatite (HA), other calcium phosphates, or other osseointegration compounds for forming a direct chemical compound between the implant and the bone. Plasma spraying and sputtering are two major techniques that have been used to deposit, for example, HA, onto an implant surface.

U.S. Patent Application Publication Nos. 2008/0220394, 2007/0110890, and 2007/0112353 disclose methods of discrete deposition of hydroxyapatite crystals to impart a nano-scale topography. Although effective, the disclosed processes require that a residual substance (i.e., HA crystals) be left on the surface post-processing to impart a nano-scale topography into the surface.

The present invention is directed to an improved implant having a submicron topography superimposed on dual micron topographies for improving the rate and extent of osseointegration and methods of making the same.

SUMMARY OF THE INVENTION

In one process described herein, a method of forming an implant to be implanted into living bone is disclosed. The implant is formed of a material comprising titanium. The method includes deforming at least a portion of a surface of the implant to produce a first micro-scale topography. The method further includes removing at least a portion of the surface to produce a second micro-scale topography superimposed on the first topography. The second micro-scale topography is generally less coarse than the first micro-scale topography. The method further includes adding a submicron topography superimposed on the first and second micro-scale topographies, the submicron topography including tube-like structures.

In another process, another method of forming an implant to be implanted into living bone is disclosed. The method includes grit blasting at least the portion of a surface of the implant to produce a first roughened surface including peak-to-valley heights of about 10 microns to about 30 microns. The method further includes acid etching the grit blasted surface to produce a second roughened surface having peak-to-valley heights of less than about 10 microns superimposed on the first roughened surface. The method further includes providing a submicron topography superimposed on the second roughened surface, the submicron topography including nanoscale tube-like structures.

In one embodiment, an implant to be implanted into living bone is disclosed. The implant is formed of a material comprising titanium. The implant includes a first micro-scale topography. The implant further includes a second micro-scale topography superimposed on the first topography. The second micro-scale topography is generally less coarse than the first micro-scale topography. The implant further includes a submicron topography superimposed on the first and second micro-scale topographies. The submicron topography includes tube-like structures.

The above summary of the present invention is not intended to represent each embodiment, or every aspect, of the present invention. This is the purpose of the figures and the detailed description which follow.

BRIEF DESCRIPTION OF THE DRAWINGS

The foregoing and other advantages of the invention will become apparent upon reading the following detailed description and upon reference to the drawings.

FIG. 2b is an insertion end view of the implant of FIG. 2a.

FIG. 3b is an insertion end view of the implant of FIG. 3a.

FIG. 4b is an end view of the implant of FIG. 4a.

FIG. 9 is a side view of an implant according to one embodiment.

FIG. 10A is a side view of an abutment for use with an implant according to one embodiment.

FIG. 10B is a cross-sectional view of the abutment in FIG. 10A.

Figure 1:
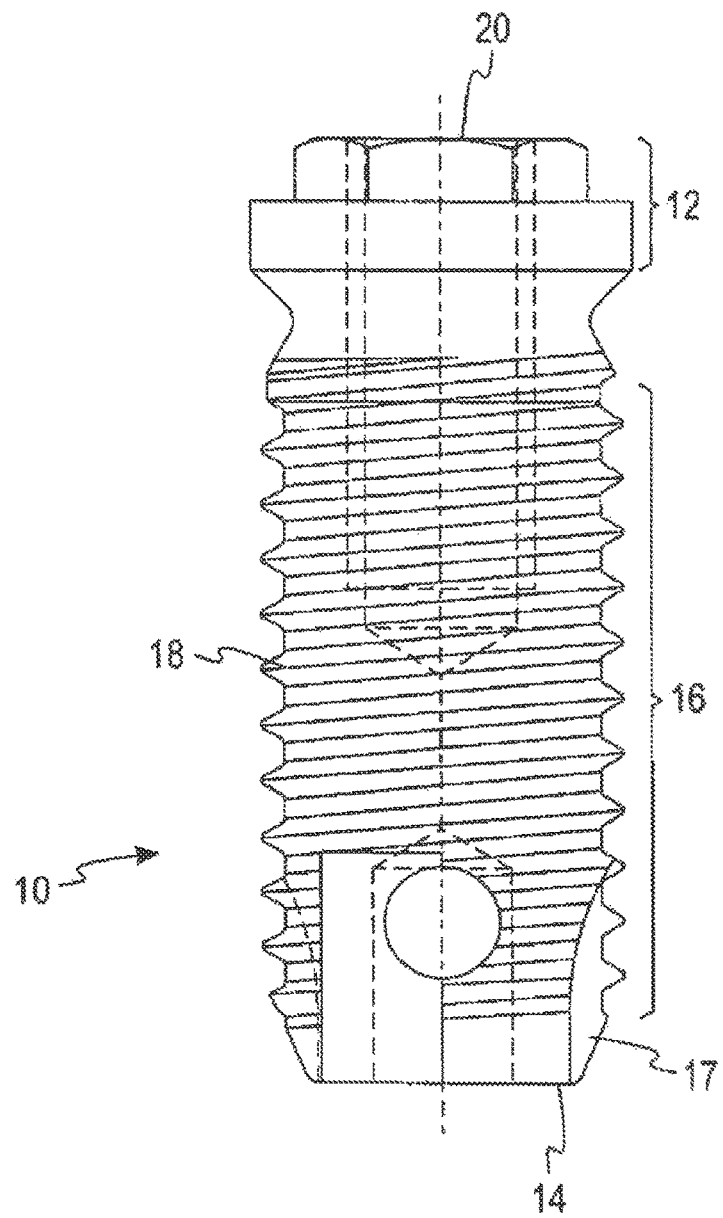
FIG. 1 is a side view of an implant according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF INVENTION

The embodiments discussed herein are directed to implants having various layers of topographical surface complexities at distinct and varied scale ranges and methods of making the same. Specifically, the implants discussed herein include topographical complexities in the coarse-micron, micron, and submicron scale ranges.

An implant in the context of the present invention means a device intended to be placed within a human body, such as to connect skeletal structures (e.g., a hip implant) or to serve as a fixture for a body part (e.g., a fixture for an artificial tooth). Although the remainder of this application is directed to dental implants, it is contemplated that the embodiments discussed herein may also be applied to other (e.g., medical) implants.

FIG. 1 shows a standard dental implant 10 that includes a head portion 12, a lowermost end 14, and a threaded bottom portion 16. The implant 10 may, for example, be made of titanium, tantalum, cobalt, chromium, stainless steel, or alloys thereof. FIGS. 2a-c, 3a-c, and 4a-b, which are discussed below, describe alternative implant designs that may also be used with the present invention.

In the implant 10 of FIG. 1, the head portion 12 includes a non-rotational feature. In the embodiment shown, the non-rotational feature includes a polygonal boss 20 that may be engageable with a tool that screws the implant 10 into bone tissue. In the illustrated embodiment, the polygonal boss 20 is hexagonal. The polygonal boss 20 may also be used for non-rotationally engaging a correspondingly shaped socket on a restorative or prosthetic component that is attached to the implant 10.

The exterior of the threaded bottom portion 16 facilitates bonding with bone or gingiva. The threaded bottom section 16 includes a thread 18 that makes a plurality of turns around the implant 10. The threaded bottom portion 16 may further include a self-tapping region with incremental cutting edges 17 that allows the implant 10 to be installed without the need for a bone tap. These incremental cutting edges 17 are described in detail in U.S. Pat. No. 5,727,943, titled "Self-Tapping, Screw-Type Dental Implant," which is incorporated by reference in its entirety.

Figure 2A:
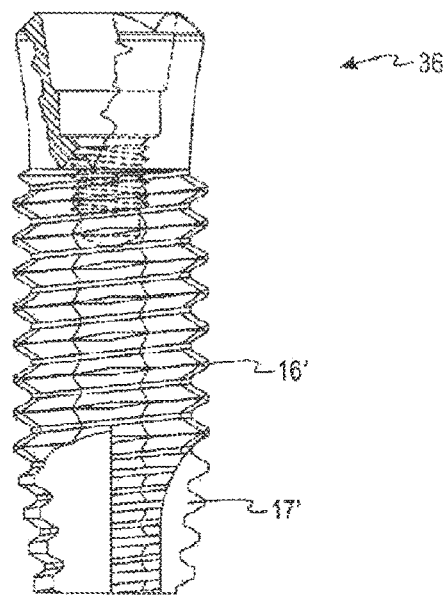
FIG. 2a is a side view of an implant according to a second embodiment.
Figure 2B:
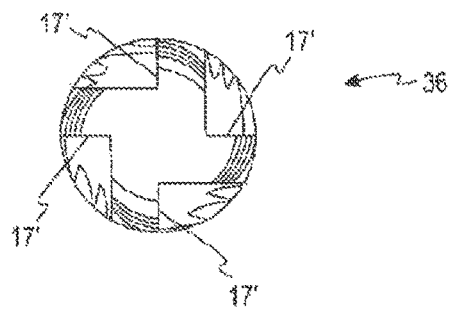
Figure 2C:
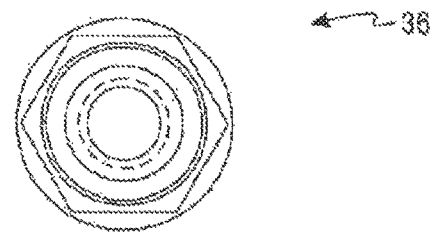
FIG. 2c is a gingival end view of the implant of FIGS. 2a, 2b.

FIGS. 2a-c disclose an implant 36 that differs from the implant 10 of FIG. 1 in the details of the cutting edges 17' and the contours of the threads defining the exterior of the threaded bottom portion 16'. When viewed in the cross-section (see FIG. 1b), the threaded outer surface 16' is non-circular in the region of the threads and/or the troughs between the threads. This type of thread structure is described in detail in U.S. Pat. No. 5,902,109, titled "Reduced Friction, Screw-Type Dental implant," which is incorporated by reference in its entirety.

Figure 3A:
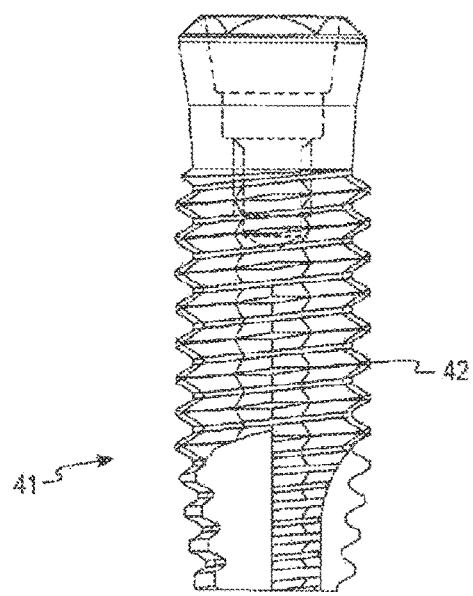
FIG. 3a is a side view of an implant according to a third embodiment.
Figure 3B:
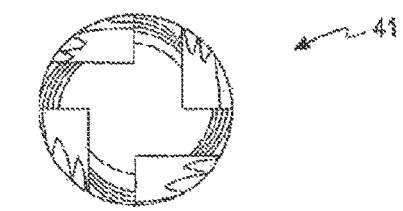
Figure 3C:
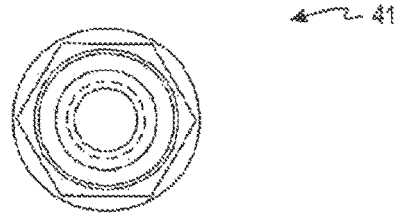
FIG. 3c is a gingival end view of the implant of FIGS. 3a, 3b.

In FIGS. 3a-c, an implant 41 having a wide diameter in the region of the threaded bottom portion 42 is illustrated. The diameter is in the range of from about 4.5 mm to about 6.0 mm with the diameter of 5.0 mm being a fairly common dimension for a wide diameter implant. Such an implant 41 is useful to engage one or both cortical bones to provide enhanced stability, especially during the period of time after installation.

Figure 4A:
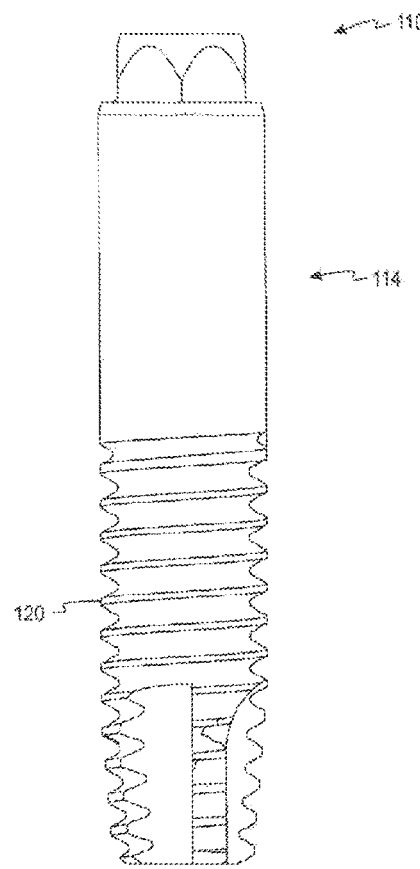
FIG. 4a is a side view of an implant according to a fourth embodiment.
Figure 4B:
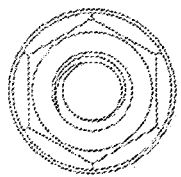

FIGS. 4a-b illustrate an implant 110 according to another embodiment that may be used with the present invention. The implant 110 includes a middle section 114 designed to extend through the gingiva. Preferably, it is a smooth surface that includes a titanium nitride coating so the underlying titanium or titanium alloy is not readily seen through the gingiva. The implant 110 also includes a threaded portion 120 that may include various thread structures and is preferably roughened to increase the osseointegration process. It is contemplated that implants other than those illustrated in FIGS. 1-4 may be used with the present invention.

According to embodiments described herein, a topographically complex implant surface including "layers" of surfaces having distinct and varied scale ranges is disclosed. The topographically complex surface generally includes a submicron roughened surface having tube-like structures superimposed onto one or more micro-scale roughened surface(s) of at least a portion (e.g., the threaded bottom portion) of the surface of an implant. "Micro-scale," as used herein, should be understood to describe an article or feature generally measured in microns such as, for example, 1 micron to 100 microns. "Submicron" or "nanoscale," as used herein, should be understood to describe an article or feature generally measured in nanometers such as, for example, 1 nanometer to 500 nanometers.

In one embodiment, the implant is a titanium or titanium alloy implant (e.g., from ELI Ti-6Al4V alloy), and the submicron tube-like structures are nanoscale titanium dioxide ($TiO_2$) tubes formed using potentiostatic anodization using an aqueous solution including fluoride ions. The attributes (e.g., height, diameter, wall thickness, spacing) of the submicron tube-like structures may be directly controlled through the manipulation of the anodization setup and preparation.

Figure 5:
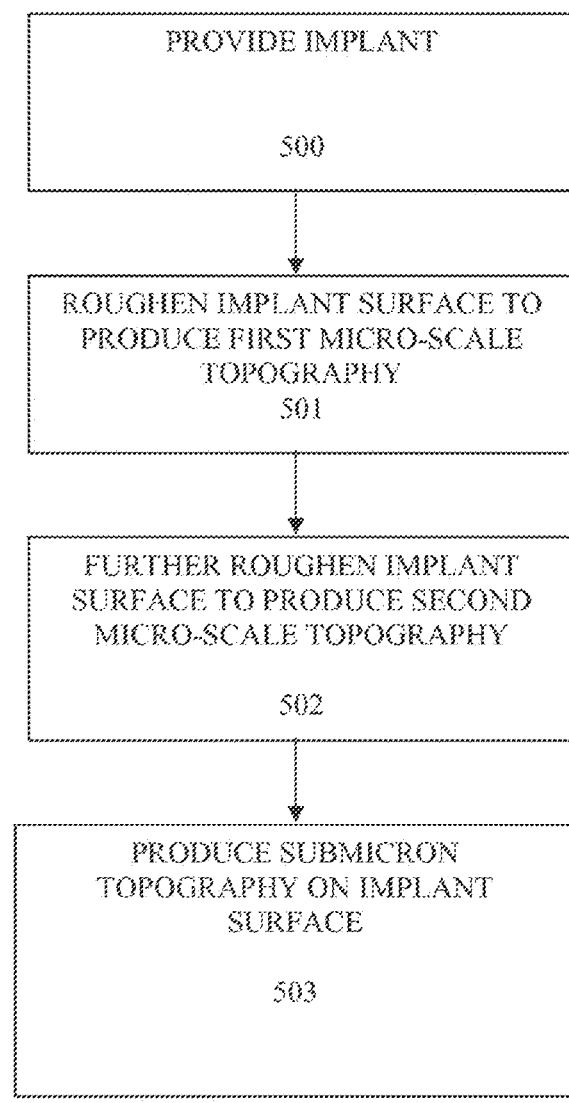
FIG. 5 is a flow diagram detailing a method of forming an implant according to an embodiment.
Figure 6:
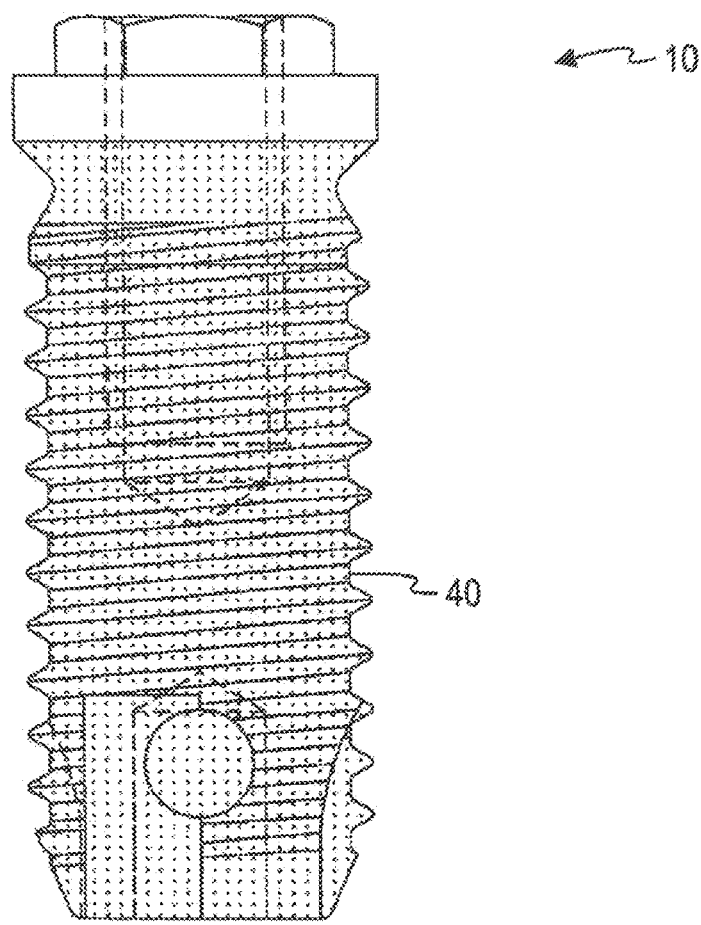
FIG. 6 is a side view of the implant in FIG. 1 with a roughened outer surface.

Turning now to FIG. 5, a general method of forming an implant is set forth according to one embodiment. At step 500, an implant is provided. At least a portion of the implant surface is roughened to form a first micro-scale topography at step 501. The roughening of step 501 may include deforming the implant surface, for example, by grit blasting, to form a coarse-micron topography. The coarse-micron topography may include peak-to-valley heights of about 1 micron to about 30 microns. In one embodiment, the coarse-micron topography includes peak-to-valley heights of about 10 microns to about 20 microns. As an example, FIG. 6 shows the implant 10 of FIG. 1 having a roughened surface 630.

At step 502, the portion of the implant surface is further roughened to form a second micro-scale topography. The second roughening step 502 may include removing/etching at least a portion of the implant surface, for example, by acid etching the implant surface, to form a fine-micron topography. The peak-to-valley heights of the fine-micron topography are generally less than about 10 microns. In one embodiment, the peak-to-valley heights range from about 1 micron to about 3 microns. The peak-to-peak distances may be less than about 3 microns.

A submicron topography including nanoscale tube-like structures may be superimposed on the first and second micro-scale topographies at step 503. The submicron topography generally includes irregular pockets of nanoscale tube-like structures that are generally consistent in height and diameter. The nanoscale topography may be formed using potentiostatic anodization using an aqueous electrolyte solution including fluoride ions to form the tube-like structures. The heights of the nanoscale tube-like structures may range from about 10 nanometers to several microns. The diameters of the nanoscale tube-like structures may range from about 10 nanometers to about 400 nanometers. In some embodiments, the nanoscale tube-like structures are fabricated from the implant's own $TiO_2$ layer. The submicron topography of step 503 assists in impacting and accelerating the early stages of osseointegration between the implant surface and adjacent bone.

The nanoscale tube-like structures are generally formed at the base of the valleys of the second micro-scale topography, leaving the second micro-scale topography generally intact. The available surface at the base of each valley of the second micro-scale topography generally dictates the size of a given cluster of tube-like structures. As such, the tube-like structures form in a generally irregular fashion. This irregularity in cluster formation is further magnified when a given surface includes the coarse-micron and fine-micron features of the first and second micro-scale topographies, respectively.

Figure 7:
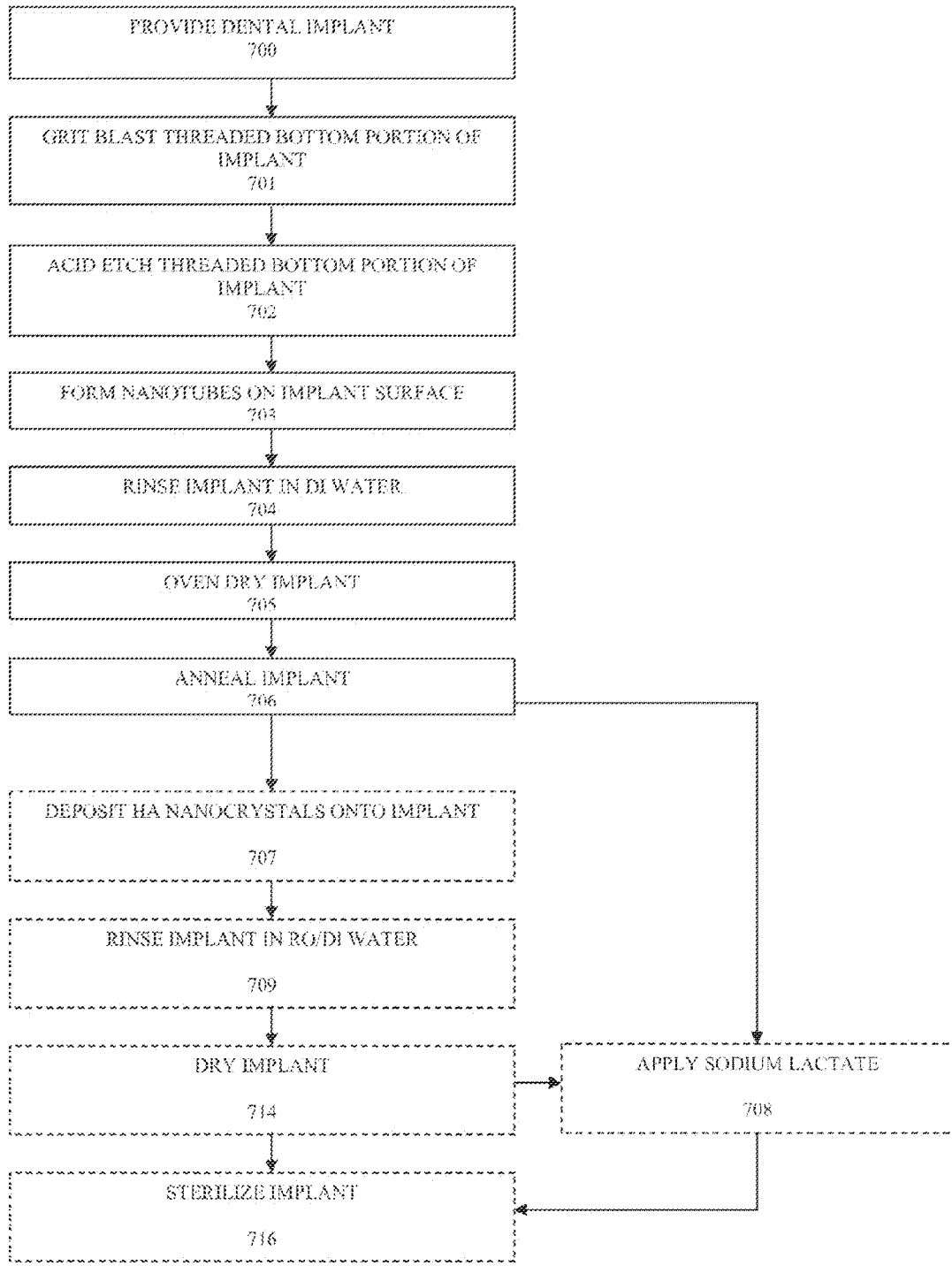
FIG. 7 is a flow diagram detailing a method of forming an implant according to another embodiment.

Referring now to FIG. 7, a more detailed method of forming an implant according to another embodiment is illustrated. A dental implant comprised of titanium (e.g., chemically pure Grade 3 (chemical) titanium) or a titanium alloy (e.g., titanium 6AL-4V ELI alloy) is provided at step 700. The dental implant may be a threaded dental implant. The surface of the implant is generally clean and dry. At least a portion of the implant (e.g., the threaded bottom portion for contacting bone) is grit blasted to form a coarse-micron topography at step 701. In one embodiment, a portion of the implant for contacting soft tissue is masked off such that it is not roughened but, rather, remains generally smooth. One non-limiting example of media that may be used to grit blast the surface includes bioresorbable hydroxyapatite (HA) media. The grit blast media may have a grain size of less than about 500 μm in size. In other embodiments, the grain size of the grit blast media used to achieve the desired surface roughness is about 180-300 μm or 300-425 μm. The coarse-micron topography may include peak-to-valley heights of about 1 micron to about 30 microns. In one embodiment, the coarse-micron topography includes peak-to-valley heights of about 10 microns to about 30 microns.

The threaded bottom portion of the implant is then acid etched to form a fine-micro-scale roughened surface at step 702. The acid etching may include removing a native oxide layer from the implant surface. The native oxide layer may be removed by a first acid solution, which may include aqueous hydrofluoric acid. The threaded bottom portion is then acid etched, which may include immersing the implant in a mixture of sulfuric and hydrochloric acids. This type of roughening method utilized on commercially pure (CP) titanium is described in detail in U.S. Pat. No. 5,876,453, titled "Implant Surface Preparation," which is incorporated by reference in its entirety. An additional roughening method utilized on Titanium 6AL-4V ELI alloy is described in detail in U.S. Pat. App. Pub. No. 2004/0265780, titled "Surface Treatment Process for Implants Made of Titanium Alloy," which is also incorporated by reference in its entirety. The peak-to-valley heights of the fine-micro-scale topography are generally less than about 10 microns. In one embodiment, the peak-to-valley heights range from about 1 micron to about 3 microns. The peak-to-peak distances may be less than about 3 microns.

It is contemplated that other surface roughening techniques may be used to achieve the desired coarse-micron and fine-micron surface topographies described herein. Such roughening techniques may include, but are not limited to, grit blasting, acid etching, titanium plasma spraying, and combinations thereof.

Grit blasting and acid etching the threaded bottom portion to form the dual-layer micro-scale roughened surface generally results in a surface including both levels of topographies, e.g., with peak-to-valley heights of less than about 10 microns superimposed on a surface having peak-to-valley heights ranging from about 10 microns to about 30 microns.

At step 703, the dual-layer micro-scale roughened surface is immersed into an aqueous electrolyte solution including fluoride ions and is exposed to potentiostatic anodization to produce a submicron topography including nanoscale tube-like structures superimposed on the dual-layer micro-scale roughened surface. The solution may include, for example, hydrofluoric acid (HF), sodium fluoride (NaF), ammonium fluoride ($NH_4F$), potassium fluoride (KF), any other compound that can produce sufficient fluoride ions in solution, combinations thereof, or the like. Generally, the potentiostatic anodization described herein results in nanoscale tube-like structures having heights of about 10 nanometers to several microns with diameters ranging from about 10 nanometers to about 400 nanometers. In one embodiment, the nanoscale tube-like structures having heights ranging from about 200 nanometers to about 400 nanometers with diameters ranging from about 75 nanometers to about 125 nanometers.

For aqueous solutions including fluoride ions, the diameters of the resulting tube-like structures are generally dependent upon the applied system voltage. The heights of the tube-like structures generally depend upon factors such as process time, aqueous solution temperature, aqueous solution content (e.g., high/low $H_2O$ content, fluoride ion source/concentration, etc.), voltage, cathode material (e.g., titanium or Pt-titanium), and the like. Variations in the characteristics of the tube-like structures range from generally flat, honeycomb-like structures to tubes having heights up to several microns.

In one example, an aqueous electrolyte solution having about 0.125 to about 0.50 w/w % hydrofluoric acid (Hfl solution may be prepared using about 49 w/w % HF stock. The solution may be kept at or near room temperature (about 23° C. to about 26° C.) throughout the anodizing process.

According to the anodizing process of one embodiment, the positive lead of a 110V power supply is connected to a fixture with a titanium implant secured thereto (anode). The negative lead of the power supply is connected to a titanium or platinum-coated titanium metal plate or mesh structure (cathode). Both the anode and the cathode are secured in a container in close proximity to one another. An electrolytic solution is poured into the container, submerging both the anode and the cathode completely. The power supply may apply a voltage ranging from about 5 volts to about 60 volts with a current of about 1 milliamp to an about 2 amp maximum output. Variations in voltage generally result in variations in the diameters of the resulting tube-like structures. In one embodiment, the power supply is set to about 20V with an about 2 amp maximum output. The power is turned on, and a voltage is applied to the system (anode, cathode, electrolyte solution) for a predetermined time (e.g., about 30 minutes±30 seconds).

At step 704, the implant is rinsed. The implant may be rinsed any suitable amount of times. In one embodiment, the implant is rinsed in two consecutive reverse osmosis (RO)/deionized water (DI) baths for about 30 seconds each. The RO/DI baths may have temperatures ranging from about 23° C. to about 26° C. The RO/DI baths represent a room temperature, drag-out rinse and a final rinse, respectively, used to remove residual solution from processing (step 703). The implant may then be rinsed in a heated RO/DI bath having a temperature ranging from about 60° C. to about 70° C. for about 30 seconds to facilitate flash drying.

At step 705, the implant may be oven dried to further facilitate flash drying of the implant. In one embodiment, the implant is placed into a forced convection oven directly following the rinse(s) of step 704. The implant may be allowed to dry in the oven for about 20 minutes to about 40 minutes. In one embodiment, the implant is dried at a temperature of about 100° C. for about 30 minutes.

At step 706, the implant is annealed in a high temperature furnace at a temperature ranging from about 475° C. to about 550° C. for about 115 minutes to about 125 minutes. In one embodiment, the implant is annealed at a temperature of about 525° C. for about 2 hours.

Hydroxyapatite (HA) nanocrystals may then optionally be deposited over and throughout the complexities of the submicron tube-like structures of the implant at step 707, thereby creating a fourth layer of topographical complexity. The HA nanocrystals may have a size ranging from about 1 nanometer to about 100 nanometers. In one embodiment, the size of the HA nanocrystals ranges from about 5 nanometers to about 20 nanometers. The HA nanocrystals may be applied as discrete nanocrystals, such that a portion(s) of the surface of the implant for contacting bone is exposed. The increase in topographical complexity—from the addition of both the submicron tube-like structures and the HA nanocrystals—further enhances the early stages of osseointegration.

The HA nanocrystals may be introduced onto the nanoscale roughened surface of the implant by immersing the implant in a solution including the HA nanoparticles. In one embodiment, the solution including the HA nanoparticles is in the form of a colloid. A representative amount of HA, in the colloid is typically in the range of about 0.01 weight percent to about 1 weight percent (e.g., 0.10 weight percent). To form the colloid, HA nanocrystals may be combined in solution with a 2-methoxyethanol solvent and ultrasonically dispersed and de-agglomerated. The pH of the colloidal solution may be adjusted with sodium hydroxide, ammonium hydroxide, or the like to a pH of about 7 to about 13. As such, the colloidal solution may include HA nanocrystals, 2-methoxyethanol, and a pH adjuster (e.g. ammonium hydroxide, and/or sodium hydroxide). This type of HA deposition is described in detail in U.S. Patent Application Publication Nos. 2007/0110890 and 2007/0112353, both titled "Deposition of Discrete Nanoparticles on an Implant Surface" and incorporated by reference in their entireties.

The implant may then be rinsed in RO/DI water to remove residual solvent and HA at step 709. The implant may be rinsed any suitable amount of times. In one embodiment, the implant is rinsed in two consecutive RO/DI baths for about 30 seconds each. The RO/DI baths may have temperatures ranging from about 23° C. to about 27° C. In one embodiment, the temperature of the rinse baths is about 25° C. The implant may then be rinsed in a heated RO/DI bath having a temperature ranging from about 60° C. to about 70° C. for about 28 to about 32 seconds.

The implant may then be dried (e.g., oven dried) to facilitate flash drying of the implant at step 714. The implant may be dried for about 20 to about 40 minutes at a temperature of about 90° C. to about 110° C. In one embodiment, the implant is placed in a forced-convection oven directly following the rinse(s) of step 709 and dried at a temperature of about 100° C. for about 30 minutes. The implant is optionally sterilized at step 716 using, for example, gamma sterilization.

Alternatively or in addition to the acts of depositing HA nanocrystals at step 707, sodium lactate or another non-toxic salt(s) may be applied over and throughout the complexities of the submicron tube-like structures and/or over the HA nanoparticles of the implant at step 708. The sodium lactate or other non-toxic salt(s) may assist in increasing the hydrophilicity of the implant surface, thereby enhancing osseointegration.

The implant surface may be characterized utilizing Field Emission Scanning Electron microscopy (FESEM). Depending upon the resolution of the instrument, the tube-like structures may typically be witnessed at magnifications of 10 kX or higher.

Example 1

Figure 8A:
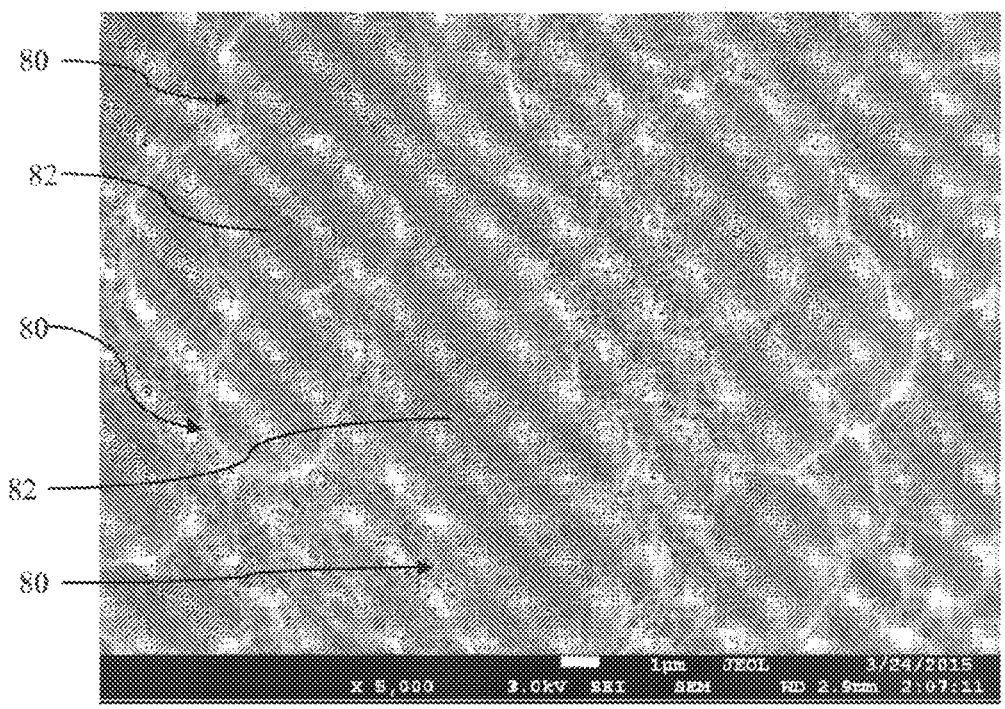
FIG. 8a is a Field Emission Scanning Electron microscopy (FESEM) image showing a commercially pure titanium having a coarse-micron topography, fine-micron topography, and submicron topography at 5 kX.
Figure 8B:
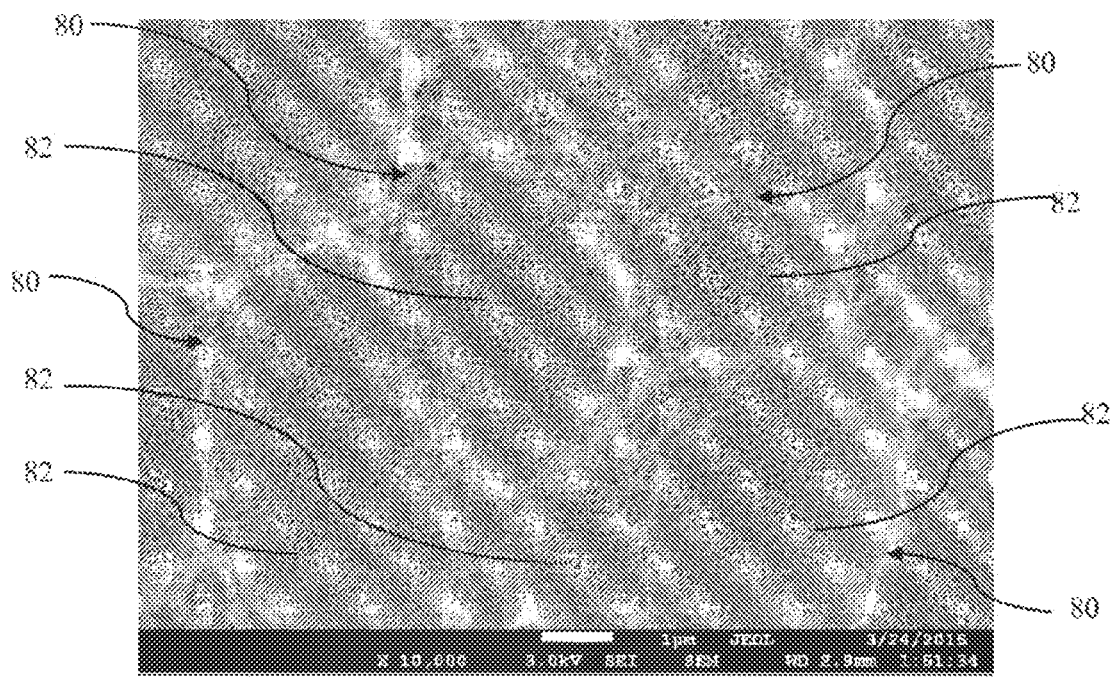
FIG. 8b is an FESEM image showing the implant of FIG. 8a at 10 kX.
Figure 8C:
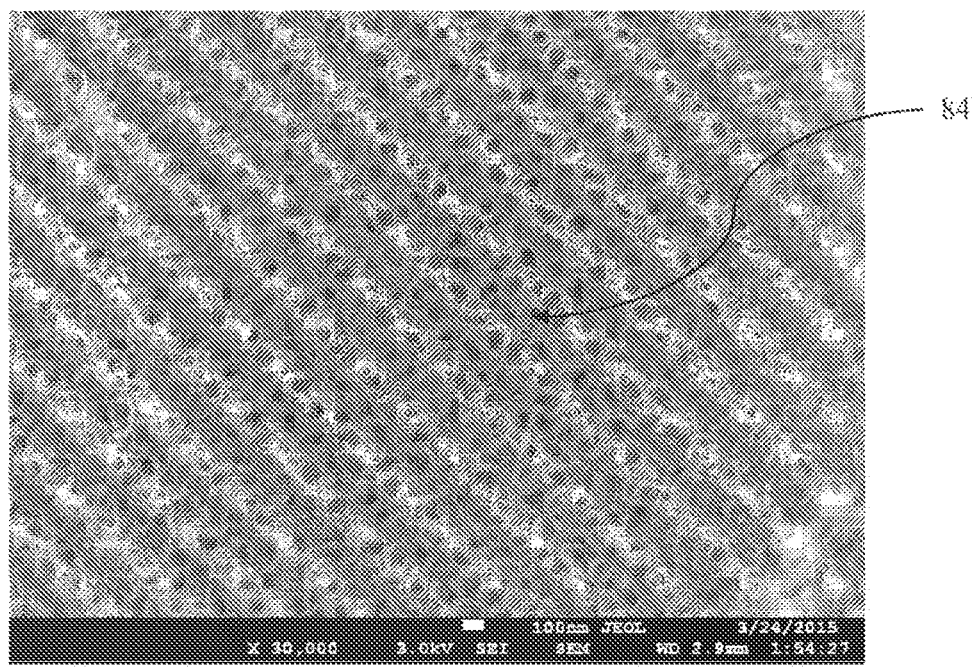
FIG. 8c is an FESEM image showing the implant of FIGS. 8a, 8b at 30 kX.

FIGS. 8a, 8b, and 8c are FESEM images showing surface complexities having a coarse-micron topography (the outer borders of which are indicated by numeral 80), a fine-micron topography 82, and a submicron topography comprising nanoscale tube-like structures 84 on a commercially pure titanium implant. The image of FIG. 8a was taken at 5 kX utilizing an FESEM. The image of FIG. 8b was taken at 10 kX utilizing an FESEM. The image of FIG. 8c was taken at 30 kX utilizing an FESEM.

The surfaces of FIGS. 8a, 8b, and 8c were formed by first grit blasting a commercially pure titanium surface with a bioresorbable hydroxyapatite (HA) media. The HA media was generally below about 500 μm in grain size. The HA media was shot at the implant surface using pressurized air in an automated blasting machine. The grit-blasted implant was then cleaned in a heated (about 50-70° C.), about 25 v/v % nitric acid ($HNO_3$) solution for about 5 minutes (±15 seconds) using ultrasonics. The implant was then immersed in three consecutive ambient (about 20-26° C.) RO/DI $H_2O$ baths for about 30 seconds (±2 seconds) each to facilitate the removal of residual acid. The implant was then dried using a forced-hot air convection oven at about 100° C. (±10° C.) for about 30 minutes (±10 minutes).

The resulting implant was then acid etched by immersing the implants in an ambient (about 20-26° C.), about 7.5 v/v % hydrofluoric acid (HF) solution for about 15 seconds (±2 seconds). The HF reacted with and removed the native titanium dioxide layer from the implant surface. The implant was then immersed in three consecutive ambient (about 20-26° C.) RO/DI $H_2O$ baths for about 2-4 seconds each to facilitate the removal of residual acid. The implant was then immersed in a heated (about 60-70° C.), sulfuric/hydrochloric acid ($H_2SO_4$/HCl) solution for about 7 minutes (±10 seconds). The acid reacted with the titanium surface and created a micron roughened topography having peak-to-peak pits ranging from about 1 μm to about 3 μm. The implant was then immersed in three consecutive ambient (about 20-26° C.) RO/DI $H_2O$ baths for about 30 seconds (±2 seconds) each to facilitate the removal of residual acid.

The implant was then dried using a forced-hot air convection oven at about 100° C. (±10° C.) for about 30 minutes (±10 minutes).

The nanoscale tube-like structures of FIGS. 8a-8c were formed using potentiostatic anodization, as discussed above, applying a voltage of about 30 volts±0.2 volts. The nanoscale tube-like structures were found to have heights ranging from about 200 to about 400 nanometer height and diameters ranging from about 75 to about 125 nanometers.

It is contemplated that various combinations of variables (e.g., applied system voltage, process time, aqueous solution content, and the like) may be used to form the desired surface attributes.

Implants formed using the methods described herein were found to have many advantages. For example, the topographically complex surface features described herein, having undercuts at specific and varied scale ranges (i.e., coarse-micron, fine-micron, and submicron), can drastically and independently influence various stages of osseointegration. Namely, osseointegration of the implants with the adjacent bone was accelerated through the increase in osteoconductive activity of early bone healing such as protein absorption, blood clot formation and retention, osteoblast recruitment (e.g., increased cell migration, proliferation), and bone bonding ability. An implant having a combination of coarse-micron, fine-micron, and submicron topographically complex surface features superimposed on one another has been shown to outperform (e.g., in mechanical disruption force testing) other implants having lesser surface complexity in both early and later time points. For example, the micron-scale roughness on at least the portion of the implant that contacts hard tissue (e.g., bone) provides increased osseointegration strength, which is accelerated by the submicron tube-like structures. Successful and prolonged implant integration favors and is dependent upon topographical complexity at distinct scale ranges.

Additionally, the implants described herein do not require any additional material to be applied thereto. Rather, the underlying micron and submicron topographies are created from the substrate (e.g., titanium) itself. As such, foreign materials do not need to be deposited onto the surface of the implant. This results in a generally more consistent topography, without, for example, the need to process and control complex stock solutions or verify (and re-verify) solution parameters (e.g., particle size analysis (PSA), concentration) for production use. Implants formed using the methods described herein are also generally less expensive to produce than those requiring additional material(s) to be deposited thereon.

Figure 11:
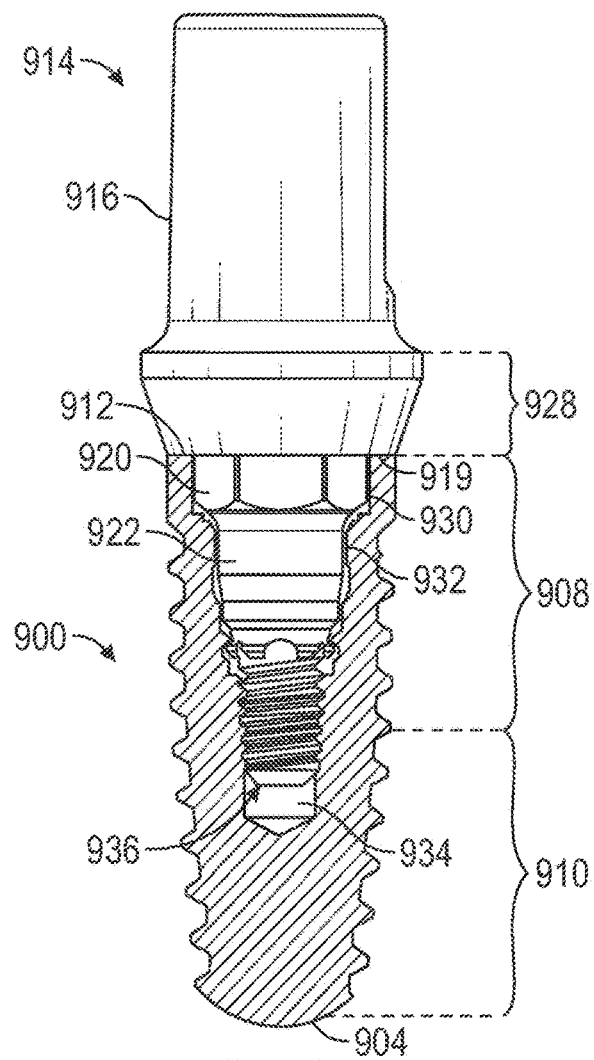
FIG. 11 is a partial cross-sectional view of the abutment in FIGS. 10A and 10B coupled to the implant in FIG. 9.

FIGS. 9-11 illustrate an implant system including an implant 900 and a mating component 914 according to another embodiment that may be used with the present invention. The implant 900 extends from a coronal end 902 to an apical end 904. The implant 900 can include threads and cutting teeth, among other features of any other implants disclosed herein. The implant can be, for example, be made of titanium, tantalum, cobalt, chromium, stainless steel, or alloys thereof. The implant 900 can include features allowing the implant 900 to be coupled to various mating components, such as, e.g., abutment, a healing abutment, a temporary or permanent prosthesis, copings, among other mating components.

The exterior of the implant 900 facilitates bonding with bone or gingiva. A portion of the implant 900 includes a thread that makes a plurality of turns around the implant 900. As shown, the threaded portion may further include a self-tapping region with incremental cutting edges that allows the implant 900 to be installed without the need for a bone tap.

Implant 900 includes two discrete layers of topographical complexities, each including one or more complexities in the coarse-micron, fine-micron, and submicron ranges, respectively. As shown in FIG. 9, implant 900 includes a first surface geometry 908 on a first portion of the surface 906 of the implant 900 and a second surface geometry 910 on a second portion of the surface 906 of the implant 900.

The second surface geometry 910 can include the previously disclosed surface complexity including a first micro-scale topography, a second micro-scale topography superimposed on the first topography where the second micro-scale topography is generally less coarse then the first micro-scale topography, and a submicron topography including tube-like structures superimposed on the first and second micro-scale topographies.

In an embodiment, the first micro-scale topography can include peak-to-valley heights of about 1 microns to about 30 microns, e.g., the first micro-scale topography can include peak-to-valley heights of about 10 microns to about 30 microns, and from about 10 microns to about 20 microns. The first micro-scale topography can be formed via girt blasting. The second micro-scale topography can be formed on the first micro-scale topography by acid etching the grit blasted surface, as discussed herein. The second micro-scale topography can include peak-to-valley heights of less than about 10 microns and peak-to-peak distances of less than about 3 microns.

The submicron topography can be superimposed on the first and second micro-scale topographies by potentiostatic anodization, as discussed herein. In an embodiment, the tube-like structures have heights in the range of about 200 nanometers to about 400 nanometers and the tube-like structures have diameters in the range of about 10 to about 400 nanometers.

A rough surface can be beneficial and can assist in bone integration when the implant 900 is implanted in bone of a patient. However, a roughness that is good for bone integration, in certain instances, can be disadvantageous for harboring bacteria. That is, the roughness can promote bacteria attachment and growth and is not beneficial for surfaces that are near where the implant 900 protrudes out of the bone and into the oral cavity. Infections near the oral cavity gum tissue can lead to peri-implantitis. Further, the greater the roughness on the implant near the oral cavity can increase the difficulty of debridement. Thus, the implant 900 in FIG. 9 has the first surface geometry 908 that differs from the second surface geometry 910. The first surface geometry 908 can include different topographical complexities such that the bone bonding benefits are still realized while minimizing the risks of bacteria growth by not having the second surface geometry 910 close to the oral cavity.

In an embodiment, the first surface geometry 908 can extend from a coronal end 902 to an intermediate point 911 along the implant 900. In one embodiment, the first surface geometry 908 can extend from about one percent (1%) to about fifty percent (50%) of a length of the implant 900. The first surface geometry 908 can extend less than about 40%, 35%, 30%, 25%, 20%, 15%, 10%, 5%, and 1% of the length of the implant. In one embodiment, the first surface geometry 908 extends at least 0.5 millimeters along the length of the implant 900 starting at the coronal end 902 and extending to the intermediate point 911. In another embodiment, the first surface geometry 908 can extend at least about 2 millimeters from the coronal end 902 to the intermediate point 911. That is, the intermediate point 911 is positioned along the 2 millimeters extending from a coronal end surface 912 of the implant 900.

In one embodiment, the first surface geometry 908 includes a submicron topography including the tube-like structures disclosed herein in another embodiment, the first surface geometry 908 includes a micro-scale topography and the submicron topography superimposed on the micro-scale topography. The micro-scale topography provided in the first surface geometry 908 can include peak-to-valley heights of less than about 10 microns and peak-to-peak distances of less than about 3 microns.

In one embodiment, the first surface geometry 908 can further include a first micro-scale topography, a second micro-scale topography, and a submicron topography. However, in this embodiment, the first micro-scale topography provided in the first surface geometry 908 should be less coarse than the first micro-scale topography in the second surface geometry 910, while the second micro-scale topography is less coarse than the first micro-scale topography in the first surface geometry 908 and the second micro-scale topography is less coarse than the first micro-scale topography in the second surface geometry 910. Stated differently, the second micro-scale topography in the first surface geometry 908 can be the same as the second micro-scale topography in the second surface geometry 908, where the first micro-scale topography in the first surface geometry 908 is less coarse then the first micro-scale topography in the second surface geometry 910.

Depending on the features of the implant 900, the coronal end surface 912 can be smooth, match the surface of the first surface geometry 908, or have a surface geometry different from the first surface geometry 908.

In one embodiment, the first and second surface geometries 908, 910 can include a first micro-scale topography that continually (or step-wise) increases from the coronal end 902 to the apical end 904 to form an increasing micro-scale topography. Thus, the roughness of the first micro-scale topography at the coronal end 902 would be less than the roughness of the first micro-scale topography at the apical end 904. In this embodiment, the implant 900 can further include a second micro-scale topography superimposed on the increasing micro-scale topography along the first and second surface geometries 908, 910. The second micro-scale topography should be less coarse than the smallest roughness provided on the increasing micro-scale topography. Further, the implant 900 can include the submicron topography including tube-like structures, where the submicron topography is superimposed on the increasing micro-scale topography and the second micro-scale topography.

FIGS. 10A and 10B show a mating component 914 that can be coupled to the implant 900. In the embodiment shown, the mating component 914 is an abutment. However, the mating component 914 can be selected from any component that may be coupled to an implant, including, but not limited to, abutments, healing abutments, scanning components, copings, temporary and permanent prosthesis, among others. FIG. 11 illustrates the implant system including the mating component 914 coupled to the implant 900.

The mating component 914 can include a post 916, a stem 918, and a transgingival portion 928. The post 916 and transgingival portion 928 can include an external surface 915, 917, respectively. In one embodiment, the stem 918 can include a non-locking portion 922 and a locking portion 920. While the non-locking portion 922 is shown as being distal of the locking portion 920, the locking portion 920 can be distal of the non-locking portion 922. The transgivingal portion 928 defines a vertical stop surface 919 that is configured to engage the coronal end surface 912 of the implant when the implant 900 is coupled to the mating component, as seen in FIG. 11.

FIG. 11 is a side view showing the mating component 914 seated in the implant 900. Part of the implant 900 is cut away to better illustrate the mating component 914 and part of the screw 936, which acts to limit axial movement of the mating component 914. The screw 936 can extend through a bore 926 (see FIG. 10B) of the mating component 914 and into a bore 934 of the implant 900. The locking portion 920 is adapted to rotationally-lockingly engage a first anti-rotation cavity 930 of the implant 900 when the mating component 914 is positioned in the implant 900. The non-locking portion 922 does not so engage a second anti-rotation cavity 932 of the implant 900. The mating component 914 is typically constructed of titanium, including alloys thereof, or titanium nitride. The mating component 914 may also be constructed of ceramic, or a variety of polymers.

In one embodiment, a portion of surfaces 915, 917 of the mating component 914 can have a surface geometry. In one example, surface 917 can include a submicron topography, as disclosed herein. In another example, surface 917 can include a micro-scale topography and a submicron topography superimposed on the micro-scale topography. In that instance, the micro-scale topography on surface 917 includes peak-to-valley heights of less than about 10 microns and peak-to-peak distances of less than about 3 microns, as disclosed herein. Providing the transgingival portion 928 with the micro-topography and/or the submicron topography helps with soft tissue attachment, which helps bond the tissue to the mating component 914 and maintains the tissue height. Further, the submicron tube-like structures promote anti-bacterial properties since the size of the tube-like structures are not favorable for bacterial growth and/or attachment. Surface 915 of the post 916 can also include a surface geometry. In the example shown in FIGS. 10A, 10B, and 11, the surface geometry of surface 915 can be the same as surface 917 or it can be different. Providing a surface geometry to the surface 915, which is configured to receive another component, can assist with, e.g., cement retention.

Figure 12:
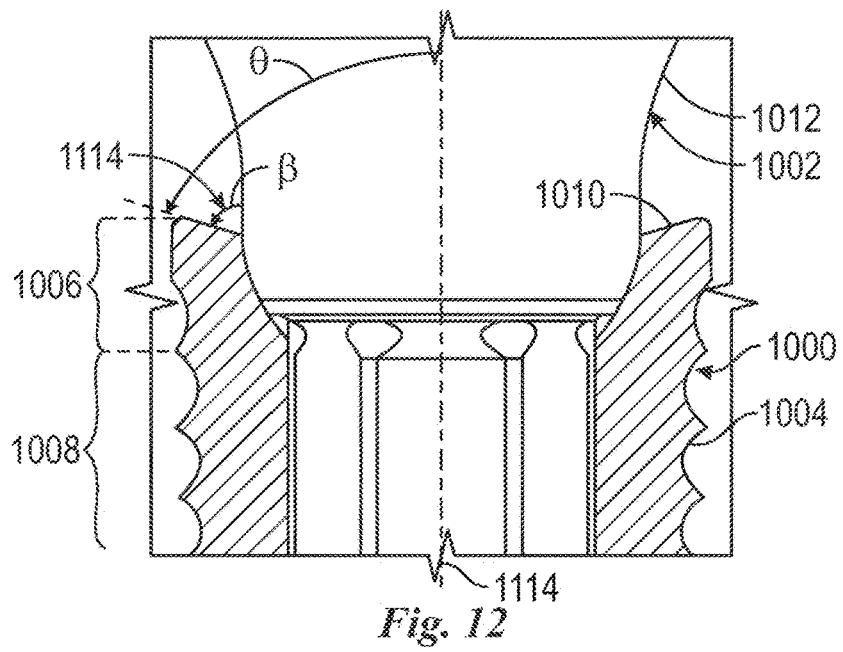
FIG. 12 is a partial cross-sectional view of an implant coupled to an abutment according to one embodiment.

While the implant system in FIG. 11 illustrates where the vertical stop surface 919 aligns with the coronal end surface 912 of the implant. FIG. 12 illustrates another implant system where an implant 1000 is coupled to mating component 1002. The implant 100 includes surface 1004 and can have a first surface geometry 1006 and a second surface geometry 1008. The first surface geometry 1006 can be the same as the first surface geometry 908 for implant 900 and the second surface geometry 1008 can be the same as the second surface geometry 910 for implant 900. As seen in FIG. 12, the mating component 1002 couples to the implant 1000 such that the mating component 1002 does not have a vertical stop surface that engages the coronal end surface of the coronal end.

As seen in FIG. 12, the proximal end of the implant 1000 includes a lateralized surface 1010 that is disposed at a negative slope relative to the central axis 1114. The negative slope is defined by an angle $\theta$. The slope is considered negative when the angle $\theta$ is less than 90°. The slope is considered positive when the angle $\theta$ is greater than 90°. As shown, the angle $\theta$ is about 45°. In another embodiment, the angle $\theta$ is between about 30° and about 60°. The lateralized surface 1010 extends circumferentially and surrounds an interior bore of the implant adapted to engage the mating component 1012, which in this embodiment is an abutment.

The mating component 1002 is typically constructed of titanium, including alloys thereof, or titanium nitride. The mating component 1002 may also be constructed of ceramic, or a variety of polymers.

In this embodiment, the surface 1012 of the mating component 1002 can have the same surface geometry as the surface 917 of the transgingival portion 928. Further, the lateralized surface 1010 can have a surface geometry that matches the surface geometry of surface 1021 of the mating component 1002.

While the embodiment in FIG. 12 illustrates a lateralized surface where the mating component 1012 is fully seated within an implant, the surface geometry of 1010 can be applied to a non-lateralized surface that is exposed to soft tissue when a mating component is coupled to the implant 1000. For example, in an embodiment where the mating component covers only a portion of a coronal end surface but not all of the coronal end surface, as shown in FIG. 11.

According to embodiments described herein, a topographically complex implant surface including "layers" of surfaces having distinct and varied scale ranges is disclosed. The topographically complex surface generally includes a submicron roughened surface having tube-like structures superimposed onto one or more micro-scale roughened surface(s) of at least a portion (e.g., the threaded bottom portion) of the surface of an implant. "Micro-scale," as used herein, should be understood to describe an article or feature generally measured in microns such as, for example, 1 micron to 100 microns. "Submicron" or "nanoscale," as used herein, should be understood to describe an article or feature generally measured in nanometers such as, for example, 1 nanometer to 500 nanometers. In one embodiment, the implant is a titanium or titanium alloy implant (e.g., from ELI Ti-6Al4V alloy), and the submicron tube-like structures are nanoscale titanium dioxide (TiC)) tubes formed using potentiostatic anodization using an aqueous solution including fluoride ions. The attributes (e.g., height, diameter, wall thickness, spacing) of the submicron tube-like structures may be directly controlled through the manipulation of the anodization setup and While the present invention has been generally described relative to the part of the implant contacting bone tissue, it is contemplated that the acts of grit blasting, acid etching, roughening, creating nanoscale tube-like structures, and depositing herein described may be performed on the entire implant.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An implant system including an implant to be implanted into living bone, the implant being formed of a material comprising titanium, the implant comprising:
   a first surface geometry on a first portion of a surface of the implant, the first surface geometry including:
   a first submicron topography including tube structures; and
   a second surface geometry on a second portion of the surface of the implant, the second surface geometry including:
   a first micro-scale topography;
   a second micro-scale topography superimposed on the first micro-scale topography, the second micro-scale topography being less coarse than the first micro-scale topography; and
   a second submicron topography superimposed on the first and second micro-scale topographies, the second submicron topography including the tube structures.

2. The implant system of claim 1, wherein the tube structures have heights in a range of about 200 nanometers to about 400 nanometers.

3. The implant system of claim 1, wherein the tube structures have diameters in a range of about 10 to about 400 nanometers.

4. The implant system of claim 1, wherein the tube structures are formed from titanium dioxide.

5. The implant system of claim 1, wherein the first micro-scale topography includes peak-to-valley heights of about 1 microns to about 30 microns.

6. The implant system of claim 5, wherein the first micro-scale topography includes peak-to-valley heights of about 10 microns to about 20 microns.

7. The implant system of claim 5, wherein the second micro-scale topography includes peak-to-valley heights of less than about 10 microns and peak-to-peak distances of less than about 3 microns.

8. The implant system of claim 7, wherein the first surface geometry on the first portion of the surface of the implant includes a third micro-scale topography, wherein the first submicron topography is superimposed on the third micro-scale topography.

9. The implant system of claim 8, wherein third micro-scale topography includes peak-to-valley heights of less than about 10 microns and peak-to-peak distances of less than about 3 microns.

10. The implant system of claim 8, wherein the first surface geometry on the first portion of the surface of the implant includes a fourth micro-scale topography, wherein the third micro-scale topography is superimposed on the fourth micro-scale topography.

11. The implant system of claim 10, wherein the fourth micro-scale topography is less coarse than the first micro-scale topography.

12. The implant system of claim 1, wherein the first surface geometry extends from a coronal end of the implant to an intermediate point.

13. The implant system of claim 1, wherein the first surface geometry extends along about fifty percent or less of a length of the implant.

14. The implant system of claim 1, wherein the second surface geometry extends from an intermediate point toward an apical end of the implant.

15. The implant system of claim 1, wherein the implant system further includes:
   a mating component configured to be coupled with the implant, the mating component including a third surface topography including one of:
   a fourth submicron topography including the tube structures; and
   a fifth micro-scale topography superimposed on fourth submicron topography.

* * * * *